United States Patent [19]

Bohan et al.

[11] Patent Number: 5,279,539
[45] Date of Patent: Jan. 18, 1994

[54] DRAWSTRING SURGICAL POUCH AND METHOD OF USE FOR PREVENTING OVARIAN ADHESIONS

[75] Inventors: John Bohan, Yardley, Pa.; Timothy J. Cunningham, Flemington; Gene W. Kammerer, East Brunswick, both of N.J.

[73] Assignee: Ethicon, Inc., Somerville, N.J.

[21] Appl. No.: 931,233

[22] Filed: Aug. 17, 1992

[51] Int. Cl.⁵ ............................................. A61F 13/00
[52] U.S. Cl. .................................... 600/37; 606/110; 606/113; 606/114
[58] Field of Search ............... 606/110, 113, 114, 127; 128/149, 849–851, DIG. 24, 749; 600/37; 604/27

[56] References Cited

U.S. PATENT DOCUMENTS

| | | | |
|---|---|---|---|
| 2,143,910 | 1/1939 | Didusch | 128/335.5 |
| 3,983,863 | 10/1976 | Janke et al. | 128/1 R |
| 4,428,375 | 1/1984 | Ellman | 128/344 R |
| 4,744,363 | 5/1988 | Hasson | 128/321 |
| 4,840,626 | 6/1989 | Linsky et al. | 604/364 |
| 4,878,890 | 11/1989 | Bilweis | 600/37 |
| 4,991,593 | 2/1991 | LeVahn | 128/856 |
| 5,002,551 | 3/1991 | Linsky et al. | 606/151 |
| 5,037,379 | 8/1991 | Clayman et al. | 600/37 |
| 5,143,082 | 9/1992 | Kindberg et al. | 128/749 |
| 5,147,371 | 9/1992 | Washington et al. | 606/127 |
| 5,176,687 | 1/1993 | Hasson et al. | 606/114 |

OTHER PUBLICATIONS

General Surgery News, 11 (10) 1990.
Davol Rubber Company Catalogue, p. 24, 1959.

Primary Examiner—David Isabella
Assistant Examiner—Debra S. Brittingham
Attorney, Agent, or Firm—Matthew S. Goodwin

[57] ABSTRACT

A medical device is disclosed for enclosing an internal bodily organ or tissue during surgery. The device is a surgical pouch with two drawstrings. The first drawstring is made up of a resilient, wire-like thread for keeping the mouth of the pouch open during use, and is detachable from the pouch. The second drawstring is intended to cinch the mouth of the pouch closed after the organ or tissue is enclosed and the first drawstring is detached. It is composed of a compliant, bioabsorbable thread.

A method of reducing or preventing post-operative ovarian adhesions is also disclosed. The method involves placing a bioabsorbable surgical pouch, especially the surgical pouch of this invention, over an ovary after a surgical procedure, and then cinching the mouth of the pouch closed to isolate the ovary from surrounding bodily tissue.

19 Claims, 7 Drawing Sheets

DRAWSTRING SURGICAL POUCH AND METHOD OF USE FOR PREVENTING OVARIAN ADHESIONS

BACKGROUND OF THE INVENTION

This invention relates to a medical device particularly well suited for endoscopic applications, which device is in the form of a surgical pouch for isolating an internal bodily organ or tissue from surrounding tissue. The invention also relates to a method of preventing certain surgical adhesions, particularly ovarian adhesions, endoscopically using a surgical pouch.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a tubular sheath, referred to as a cannula, after puncture through the wall of the body cavity with a trocar, which is a sharp-pointed instrument. The surgeon can then perform diagnostic and therapeutic procedures at the surgical site with the aid of specialized instrumentation designed to fit through additional cannulas providing openings into the desired body cavity as may be required.

In many surgical procedures, including those involved in endoscopic surgery, it is often necessary to isolate bodily tissue or organs from the surrounding tissue at the surgical site, so that surgical procedures can be performed without fear of contamination. This is especially challenging during endoscopic surgery because of the small openings through which such tissue or organs must be isolated.

In response to this need for medical devices to isolate bodily tissue endoscopically, numerous devices have recently been developed. The driving force behind the development of these devices has been the need to not only isolate tissue but also remove it once the tissue is isolated. Under these circumstances, it is necessary to fragment, or morcellate, the bodily tissue so that it can be readily removed through the small endoscopic openings.

The most effective devices recently developed for isolating and removing tissue endoscopically are surgical drawstring bags capable of being closed remotely from the surgical site. One such drawstring bag is disclosed in U.S. Pat. No. 5,037,379, in which the drawstring is long enough to allow the surgeon to grasp a looped portion of the drawstring outside of the body even after the bag has enclosed the desired bodily tissue at the internal surgical site. The surgeon can then use the looped drawstring portion to close the bag, and to pull the bag up through the cannula to remove the bag and its fragmented tissue contents when the surgical procedure is completed.

Another more sophisticated surgical drawstring device is disclosed in U.S. Ser. No. 679,893, filed Apr. 3, 1991. This device couples the benefits of a ligating instrument designed to ligate remote blood vessels endoscopically with a surgical bag for ensnaring bodily tissue. It represents an advantage over the device described in the '379 patent because the device is easier to insert through a cannula, to maneuver once it is within the body cavity, and to remove when the surgical procedure is completed.

The surgical drawstring bags referred to above have been designed to be used in combination with an endoscopic instrument for removing tissue. This instrument is called a tissue morcellator, and its use with a surgical bag is described in an article in General Surgery News, 11 (10) 1990. This article illustrates the feasibility of laparoscopic nephrectomy, which is an endoscopic procedure for excising a kidney, by first enclosing the desired kidney in a nylon drawstring entrapment sack and then using a tissue morcellator to fragment and aspirate the kidney from the sack.

Even older designs of drawstring surgical bags could be modified for use in endoscopic procedures. For example, page 24 the 1959 Davol Rubber Company catalogue describes a drawstring surgical bag for isolating the small bowel. Another interesting concept is described in U.S. Pat. No. 4,428,375. This patent describes a drawstring mesh or net bag for encapsulating a fractured organ, particularly a traumatized spleen, during surgical repair. The bag is intended to conform to the organ shape and compress the organ sufficiently to close any organ fractures and provide hemostasis. The bag has a plurality of drawstrings to aid in conforming the bag to the organ. Similar type devices for enclosing fractured or damaged organs are described in U.S. Pat. Nos. 4,878,890; 2,143,910 and 3,983,863.

Finally, U.S. Pat. No. 4,991,593 describes a flexible surgical bag for enclosing a body organ. The bag provides means for limiting the closure of the bag to prevent injury to the enclosed body organ.

While all of these surgical bags simplify and facilitate numerous surgical procedures, including endoscopic procedures, the surgical bags of the prior art suffer from a major drawback. Specifically, none of the surgical bags disclosed are well adapted for use during an endoscopic technique in which the bag is to remain intact after surgery is completed. Ideally, implantable surgical devices, including surgical bags, are bioabsorbable when exposed to moist bodily tissue to prevent contamination or unwanted tissue reaction. In other words, when such a bag has accomplished its task, it is desirable in certain instances for the material from which the bag is composed to break down into small components which can be readily passed through the system without undesirable side effects.

Even though the prior art has described the use of bioabsorbable surgical bags (see, for example, U.S. Ser. No. 679,893, filed Apr. 3, 1991), the drawstring closure means described for those bags is ill-suited for endoscopic surgical techniques. Most of the bags described in the art utilize relatively rigid, nonabsorbable threads as the drawstrings for the bag, regardless whether the bag is intended to be bioabsorbable or nonabsorbable. The use of such a drawstring thread has found widespread acceptance because its relative rigidity helps to keep the mouth of the bag open, which is very important when working in an endoscopic field, and the surgeon needs the ability to place the desired body organ or tissue inside the bag.

Unfortunately, the use of rigid, nonabsorbable drawstring threads for surgical bags is unacceptable because such a thread could easily cause adverse tissue reaction since it remains indefinitely within the bodily tissue. Alternatively, the descriptions for the prior art drawstring bags include the potential use of absorbable threads in conjunction with the bag. While the combination of an absorbable thread drawstring with the bag would be particularly desirable when the drawstring bag is intended to remain intact at the surgical site, desirable absorbable threads are by nature very compliant and limp. These absorbable threads would not have the properties required to keep the mouth of the bag open before closure. This creates a particularly cumbersome problem for the surgeon during endoscopic surgery, because it then becomes much more difficult for the surgeon to place the desired bodily organ or tissue inside the bag when the mouth of the bag fails to remain open. For these reasons, a new surgical drawstring bag is needed to accommodate those applications where it is desired to use a bioabsorbable bag during endoscopic surgery.

In other endoscopic surgical procedures, it is often necessary or desired to prevent surgical adhesions. Adhesions are unwanted tissue growth which occurs following surgery from the manipulation of tissue, or the rubbing together of organs during the surgical procedure. Numerous methods have been described to prevent the occurrence of adhesions, one of them being the placement of an absorbable barrier fabric between layers of adjacent tissue or organs to prevent unwanted tissue growth following surgery. See, for example, U.S. Pat. Nos. 4,840,626 and 5,002,551.

A particularly significant problem caused by surgical adhesions is infertility when adhesions form on the ovaries. While the use of the barrier fabrics described in the patents of the preceding paragraph is acceptable for preventing adhesions at numerous locations within the body, the prevention of adhesions with such a barrier fabric on the ovaries is especially difficult because of the shape of the ovary. Since the ovary is generally round in shape, it is practically impossible to effectively cover the entire surface area of the ovary with the flat, rectangular-shaped barrier fabric described above. In view of the problem still remaining with preventing adhesions during surgery, particularly ovarian adhesions, it would be helpful to the medical community if a medical device could be developed that would facilitate the prevention of such adhesions.

In view of the deficiencies inherent in the prior art drawstring surgical bags and their use, particularly bags which are to remain intact within the bodily tissue following surgery, it would be desirable to have a drawstring surgical bag which is particularly well suited for endoscopic applications requiring the bioabsorption of the bag and its drawstrings. More specifically, what is needed is such a surgical drawstring bag whose mouth can remain open without difficulty when a bodily organ or tissue is desired to be implanted within the bag, yet will not cause inflammatory or toxic reactions to tissue when the bag remains in place after surgery. Additionally, it would be particularly desirable if a method could be developed for use in combination with a drawstring bag for preventing ovarian adhesions.

SUMMARY OF THE INVENTION

In one aspect, the invention is a medical device for enclosing an internal bodily organ or tissue during surgery. The device comprises a surgical pouch having first and second drawstrings attached to the pouch. The first drawstring is detachable from the pouch, and is made of a resilient, wire-like thread for keeping the mouth of the pouch open during use. The second drawstring is made of a compliant, absorbable thread for cinching the mouth of the pouch closed after the organ or tissue is enclosed, and the first drawstring is detached from the pouch.

Surprisingly, this device is particularly well suited for use during endoscopic surgery when the device is intended to remain intact at the surgical site following surgery. The first drawstring of the surgical pouch keeps the mouth of the pouch open during use, so that the surgeon need not worry about how to keep the mouth open when he attempts to place the body organ or tissue inside the pouch. Since such a thread would typically remain indefinitely inside the body, and therefore cause adverse tissue reaction and potential trauma, the second drawstring is provided for cinching the mouth of the pouch once the first drawstring is detached and the organ or tissue is enclosed inside the pouch. In this manner, what remains behind after surgery is simply the biodegradable pouch in combination with an absorbable thread which will not cause adverse tissue reaction. Therefore, the pouch can be used most effectively through small endoscopic openings without worry caused by the fear of adverse tissue reaction when the surgery is complete and the pouch remains in the body.

In another aspect of the invention, the invention is a method of reducing or preventing post-operative ovarian adhesions. The method comprises the following steps: a) placing a bioabsorbable surgical pouch over an ovary after a surgical procedure, and then b) cinching the mouth of the pouch closed so as to isolate the ovary from surrounding bodily tissue.

This method is particularly well-suited for preventing ovarian adhesions, because the entire ovary is enveloped by the pouch. This has the tremendous advantage over the use of the barrier fabrics described in the prior art because the use of such fabrics cannot readily completely isolate the ovary from surrounding tissue. However, using the pouch in the method of this invention avoids this problem in a very simplistic manner.

DETAILED DESCRIPTION OF THE PREFERRED EMBODIMENT

As used in this specification, the word "distal" is used to describe that portion of the device which extends away from the user during use, and the word "proximal" is used to describe that portion of the device that extends toward the user during use. Similarly, "distally" refers to movement extending away from the user during use of the device, and "proximally" refers to movement extending toward the user.

Figure 1:
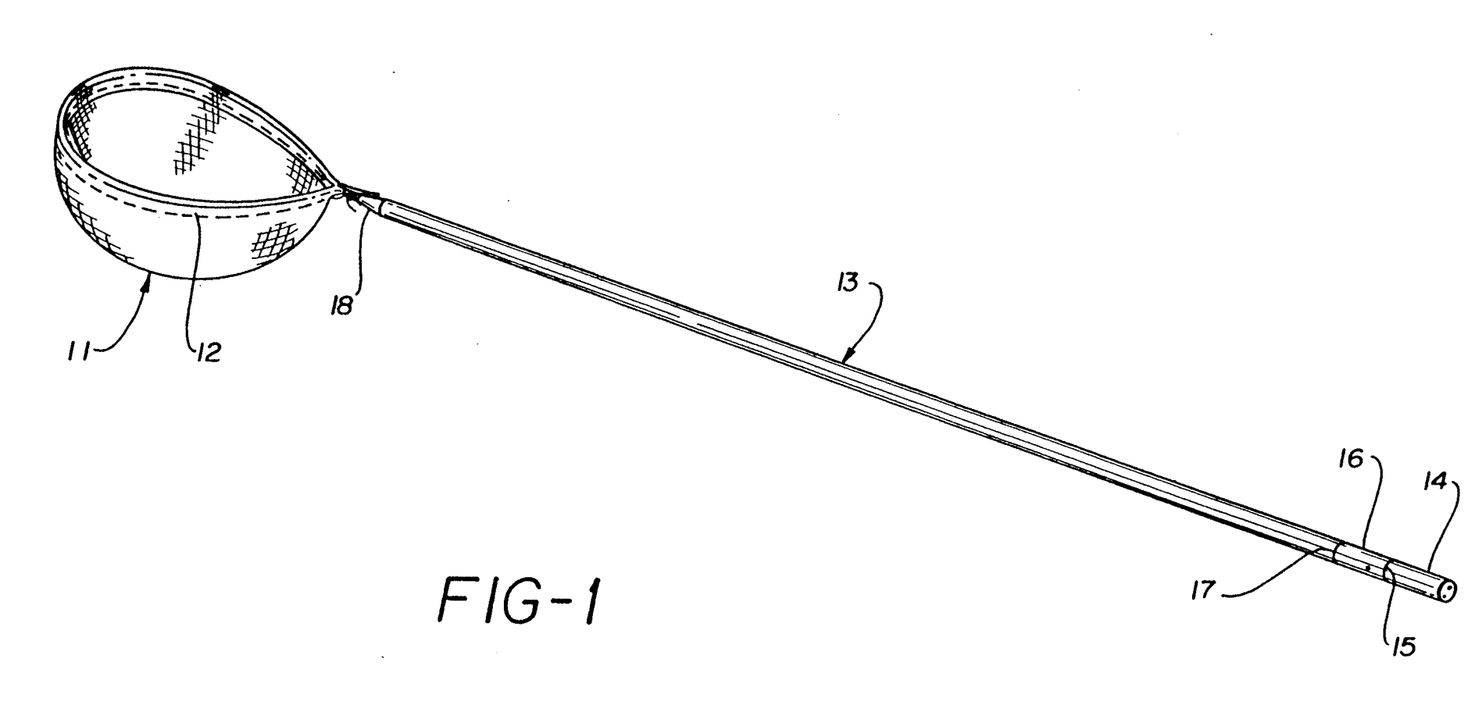
FIG. 1 is a perspective view of the most preferred medical device of this invention.
Figure 2:
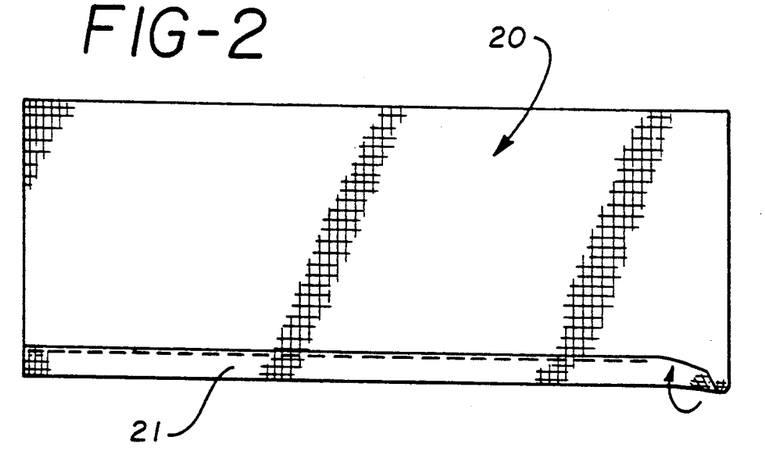
FIGS. 2-5 are plan views showing the method of forming the surgical pouch which makes up part of the medical device.
Figure 3:
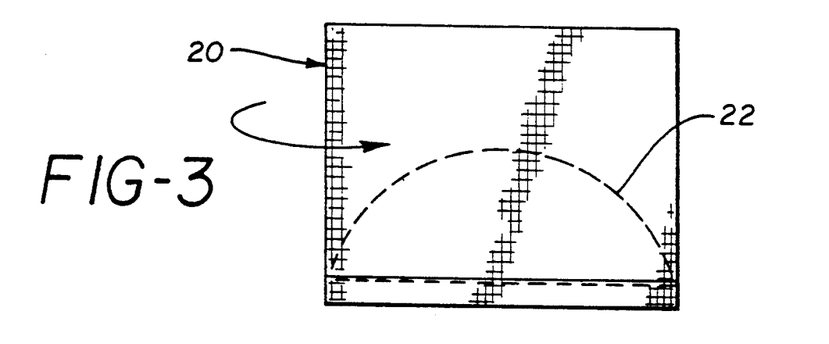
Figure 4:
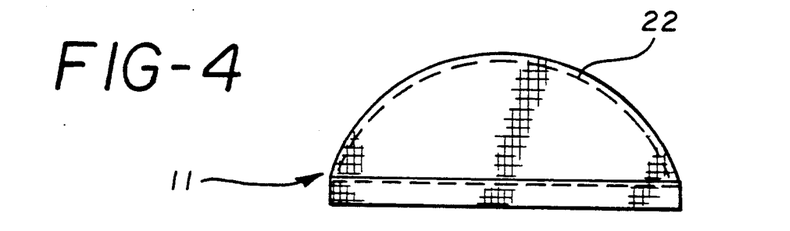
Figure 5:
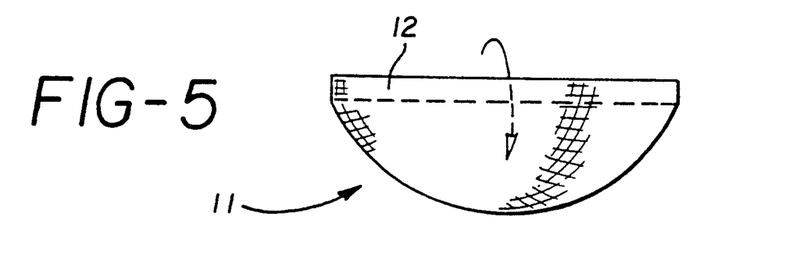

Referring to FIG. 1, the medical device has a bioabsorbable pouch 11. The pouch has a stitched hem 12 bordering the periphery of the mouth of the pouch. The hem encloses the first and second drawstrings of the device, as will be explained in more detail in reference to the remaining drawings. The drawstrings are threaded through cannula 13. The cannula has a first frangible portion 14, which is demarcated by score line 15. The cannula also has a second frangible portion 16, which is demarcated by a second score line 17. The first and second frangible portions of the cannula are broken away from the remainder of the cannula during the sequence of steps for enclosing a bodily organ, and allow for cinching the mouth of the pouch closed from a position which is remote from the pouch itself. The cannula also includes a tapered distal end 18.

Referring now to FIGS. 2-5 in combination, the pouch can be formed by first sewing a hem 21 with an absorbable thread across the bottom of a sheet 20 of the desired bioabsorbable material. The sheet is then folded in half, and an arcuate row 22 of stitches is placed on the pouch material. The extraneous sheet material is subsequently removed, and the pouch is turned inside out.

For purposes of defining this invention, the pouch is "bioabsorbable" if it is capable of breaking down into small, non-toxic segments which can be metabolized or eliminated from the body without harm. Complete degradation of the pouch may take several months, although preferably it will completely degrade within 12 months and most preferably within six months. Advantageously, the pouch will not completely degrade before 10 days. Otherwise, it may be possible for adhesions to form on the surrounded tissue after the pouch has degraded.

The preferred bioabsorbable pouch for preventing post-operative ovarian adhesions is a pouch which is constructed of a warp knit fabric. Therefore, the sheet material shown in FIG. 2 from which the pouch is formed is composed of this fabric material. Preferably, the fabric is composed of oxidized regenerated cellulose, and is characterized by having a density of 8.0 to 15 mg/cm$^2$ and a porosity of 12-20% open area. These kinds of warp knit fabrics are described in detail in U.S. Pat. No. 5,002,551, incorporated by reference herein. Additionally, the pouch material may be impregnated with heparin, which has been found to further enhance the effectiveness of the warp knit fabric material to reduce or prevent adhesions, as further described in U.S. Pat. No. 4,840,626. Furthermore, the fabric, which may be acidic in nature, can be neutralized to render it even more compatible with bodily tissue by using the neutralization process described in U.S. Pat. No. 5,134,229.

Figure 6:
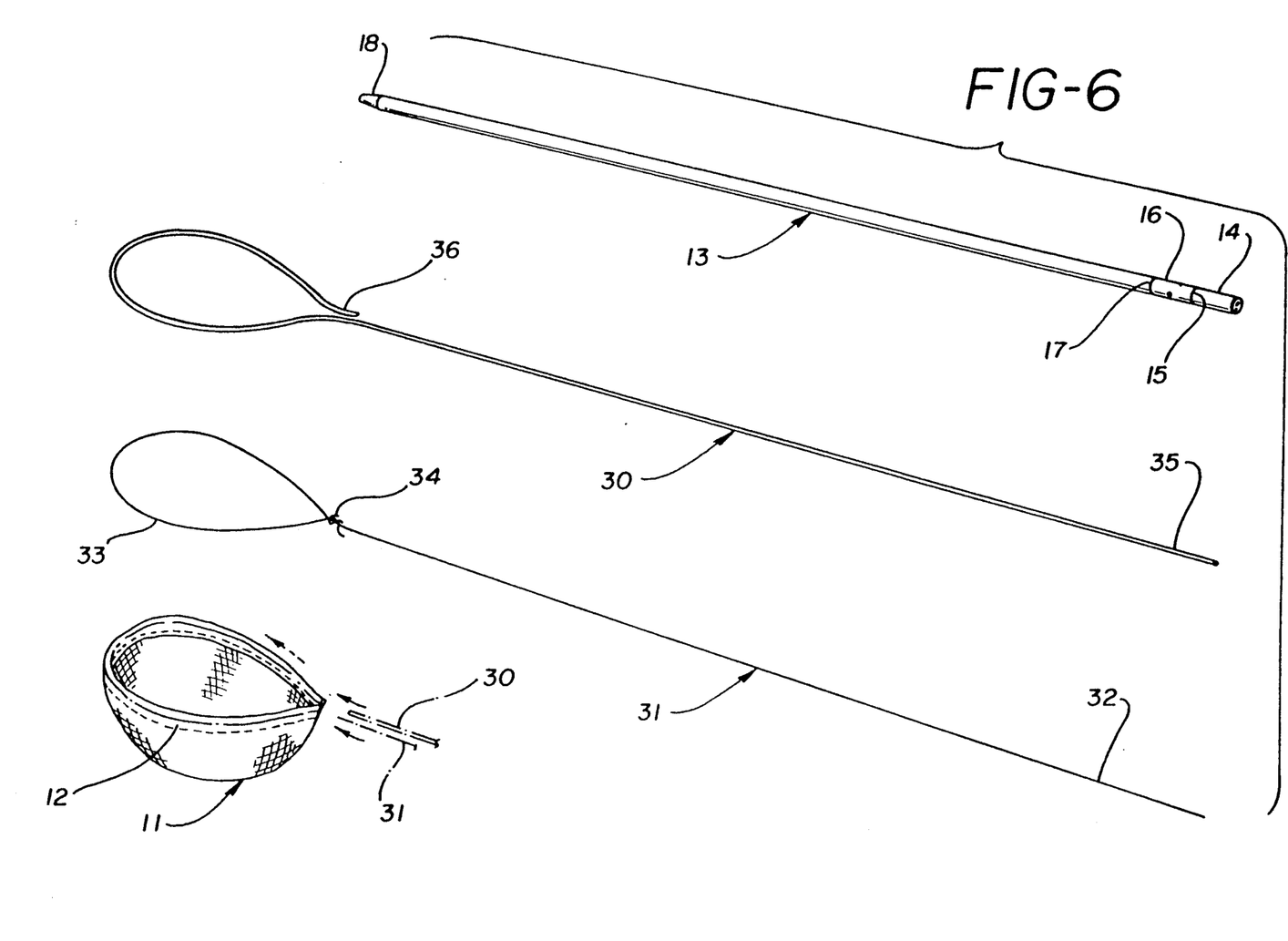
FIG. 6 is an exploded perspective view of the first and second drawstrings of the medical device, and their structural relationship to the cannula and the surgical pouch of the preferred medical device.

The interrelationship of the first and second drawstrings with the pouch and the cannula is illustrated in FIG. 6. First drawstring 30 is threaded through hem 12 of the pouch. The distal end of the first drawstring is then glued to the tapered distal end 18 of the cannula to form a severing end 36 (illustrated in further detail at FIG. 7). The severing end of the first drawstring is subsequently cut from the distal end of the cannula when the device is used so it can be detached from the pouch. The proximal end of the first drawstring is threaded through the cannula to form pulling end 35 of the first drawstring.

In a similar manner, the second drawstring 31 is threaded through hem 12 of the pouch. Once it is threaded through the hem, a slip knot 34 is tied to form a distal loop 33, and the remainder of the second drawstring is threaded through the cannula to form a slide end 32. The slip knot is configured to allow sliding movement of slide end 32 proximally and to prevent distal loop 33 from loosening when the mouth of the pouch is cinched closed. In a preferred embodiment, a second knot can be added to the distal loop in close proximity to the slip knot. This second knot could be generally a simple throw, and is designed to limit the cinching of the loop. This is done to prevent the loop from becoming too tight around a delicate body organ, for example, an ovarian ligament, when the mouth of the pouch is cinched closed. In this way, the tightened loop does not strangle the ligament.

The first drawstring is preferably made up of a thread which possesses the requisite wire-like properties to keep the mouth of the pouch in an open position during surgery. Preferably, this thread is a non-absorbable thread. It is advantageously composed of nylon, polyester or polypropylene.

If desired, a portion of the cannula can be threaded through the hem to further support the mouth of the pouch in the open position. This may also be advantageous because it may be easier to push and guide the pouch during surgery. When the mouth of the pouch is ready to be cinched closed about a desired body organ, the cannula can easily be removed from the hem.

The second drawstring is preferably a compliant, limp bioabsorbable thread. Although any bio-absorbable thread can be used so long as it has the requisite limpness, the thread is preferably composed of a polymer of a lactone monomer or mixture of lactone monomers. For example, the bioabsorbable thread may be composed of a polymer of p-dioxanone, glycolide, lactide, trimethylene carbonate, $\epsilon$-caprolactone, or a copolymer of any of these lactone monomers. In addition, this thread can be composed of oxygenated regenerated cellulose, and therefore can be composed of the same material as that of the pouch. The required limpness for such threads can be obtained by using a finely sized thread, for example, a size 4-0 thread.

Figures 7, 7A:
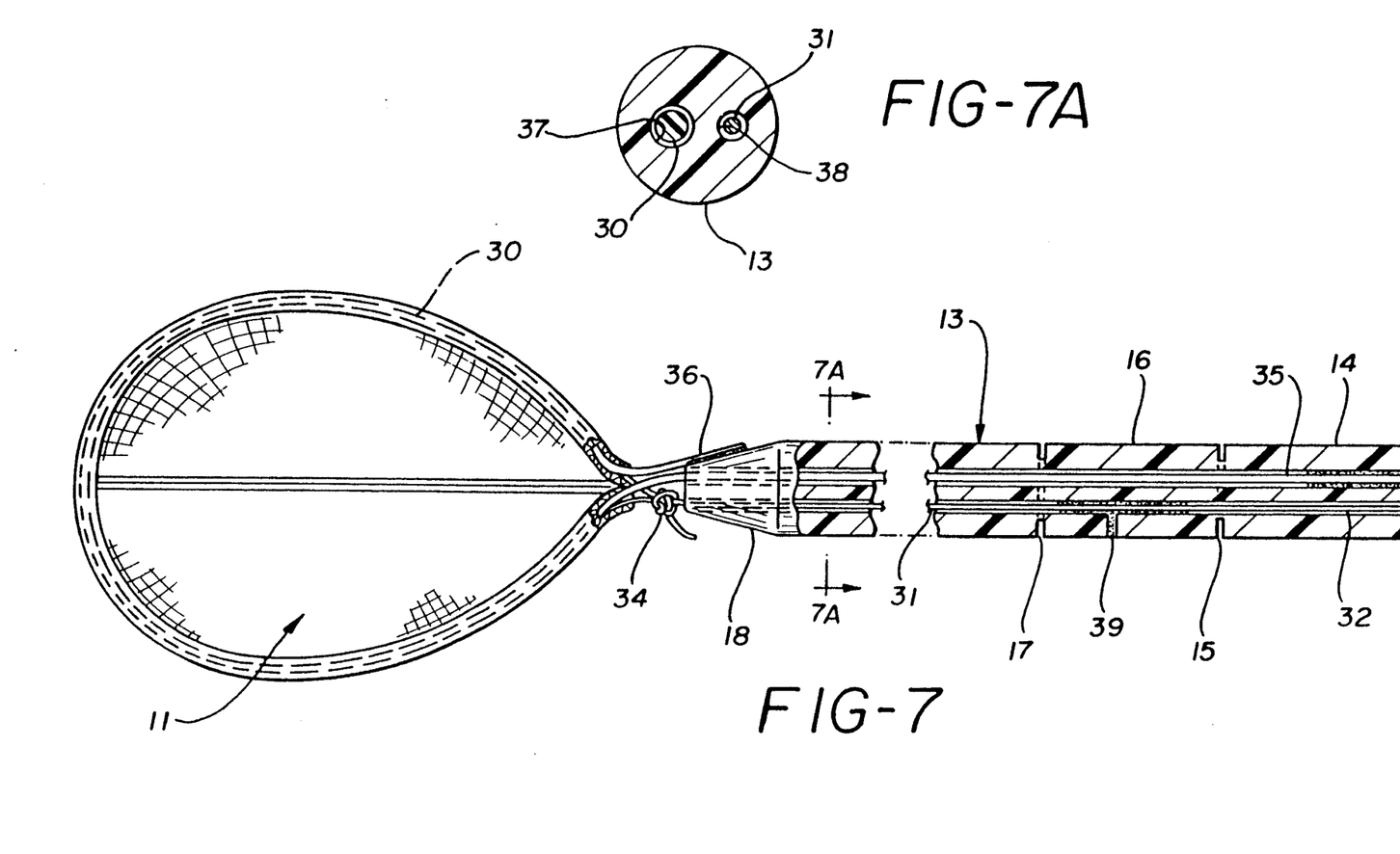
FIG. 7 is an enlarged top plan view in partial cross section of the medical device shown in FIG. 1.
FIG. 7a is a cross-sectional view taken along line 7a—7a of FIG. 7.

FIG. 7 presents a good detailed view of the drawstrings threaded through, and attached to, the cannula. The severing end 36 of the first drawstring is glued to the tapered distal end 18 of the cannula 13, and the pulling end 35 is glued to the proximal end of the cannula within the first frangible portion 14 of the cannula. The second drawstring is glued inside the cannula within the second frangible portion 16. The glue for attaching the second drawstring within the second frangible portion can be added, for example, by filling the second frangible portion with glue through glue port 39. As shown in more detail in FIG. 7a, each of the drawstrings is threaded through the cannula in separate and distinct first and second channels, 37 and 38, respectively. Thus, the cannula is a dual channel cannula.

Figure 8:
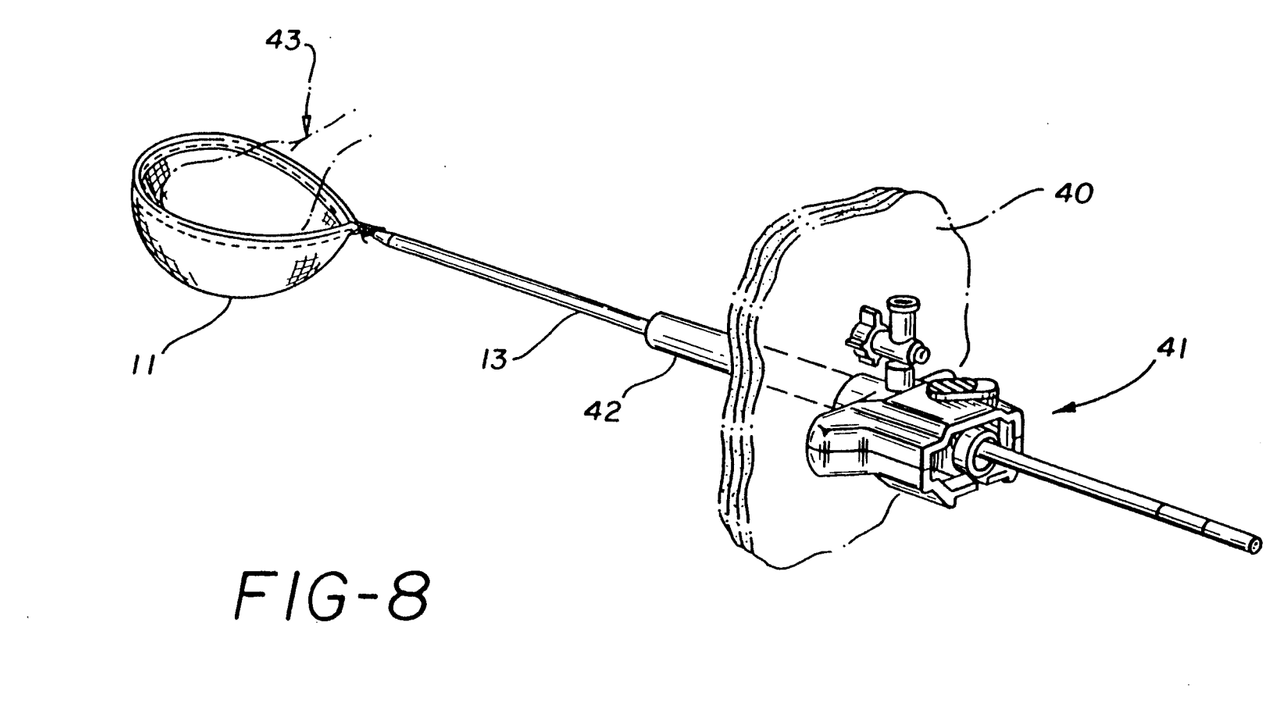
FIGS. 8-12 are perspective views showing the sequence of steps for enclosing a bodily organ or tissue with the preferred medical device.
Figures 9, 10:
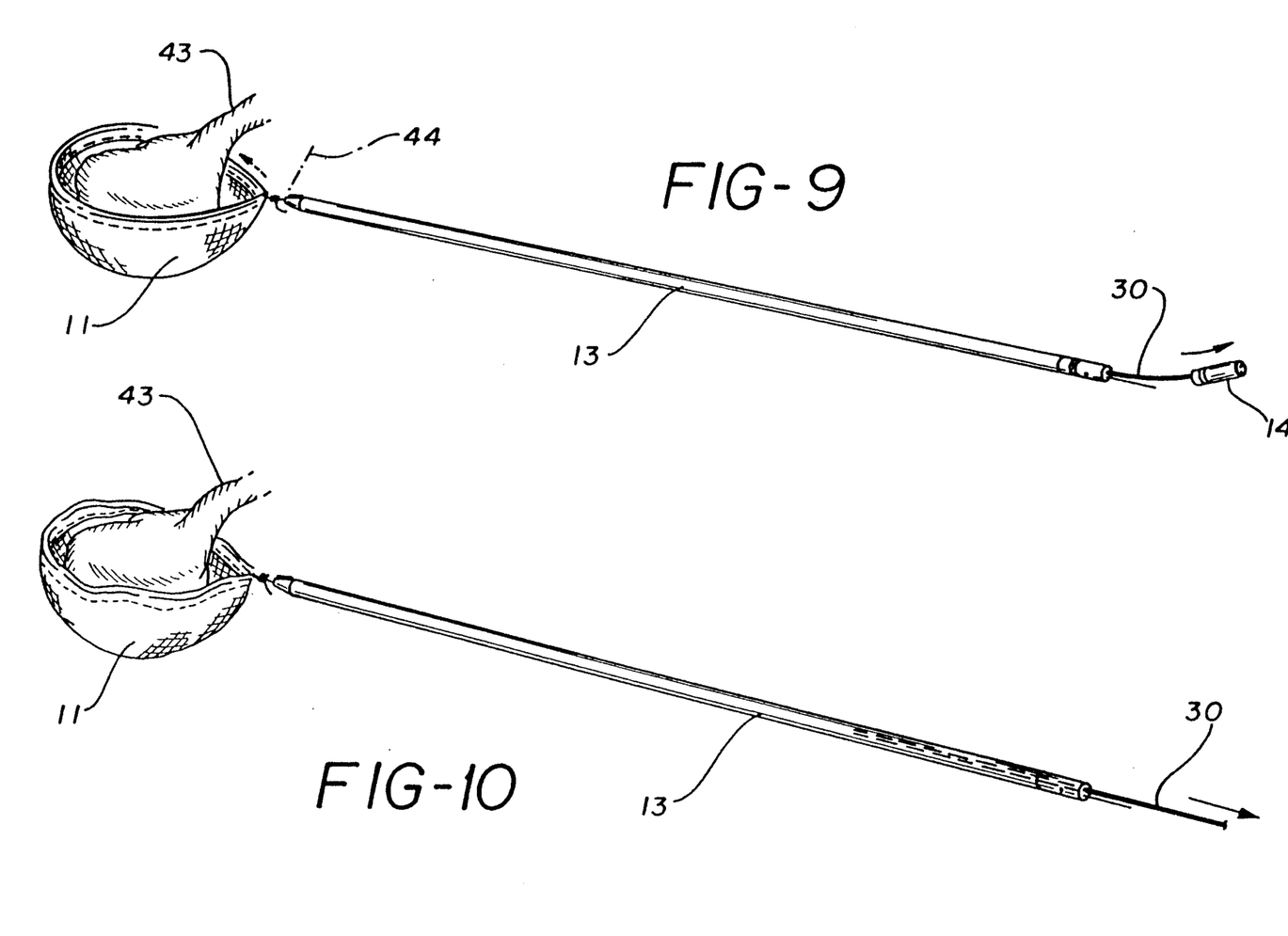

The relatively small cross-sectional diameter of the cannula, and the foldable nature of the pouch, make the use of this medical device well-suited for endoscopic applications. As shown in FIG. 8, the device may be placed down a trocar 41 to penetrate bodily tissue 40 as it enters the desired bodily cavity through the trocar cannula 42. Once the device is within the desired body cavity, the internal bodily organ or tissue, preferably an ovary 43, can be placed inside the pouch.

Referring now to FIGS. 9–12 in combination, once the user of the device has placed ovary 43 inside the bag, the user would then cut the severing end 36 (not shown) of the first drawstring 30, at the location of the first cutting line 44. Once the first drawstring has been cut, the user would then snap off the first frangible portion 14 of the cannula and pull it proximally. When this frangible portion is pulled, the first drawstring is consequently pulled from the hem of the pouch 11, and then through the cannula.

Figures 11, 12:
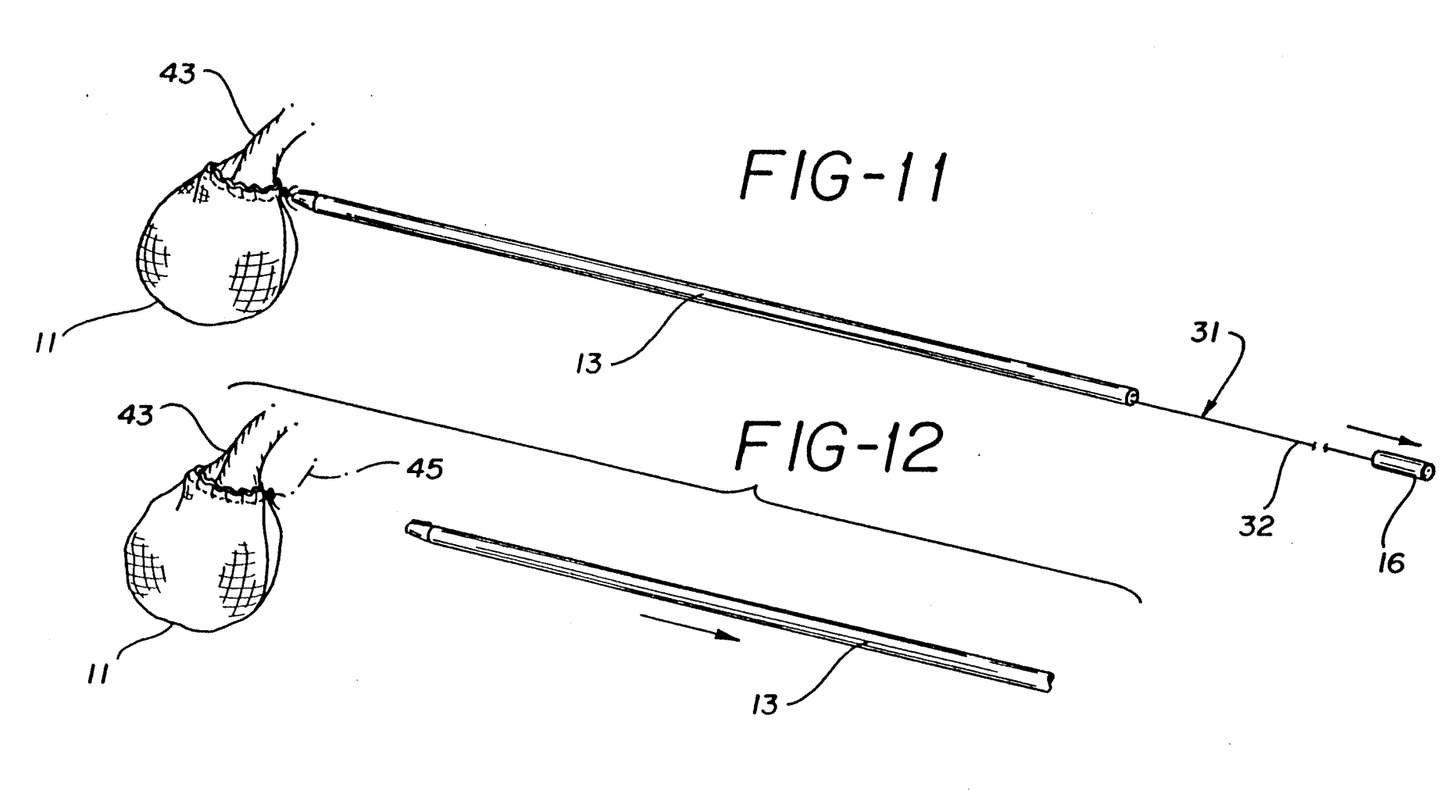

Once the first drawstring is completely removed, the mouth of the pouch can then be cinched closed with the second drawstring. Referring now to FIG. 11, the user would first snap off the second frangible portion 16 of the cannula, and then pull it proximally. When the second frangible portion is pulled away, the slip knot on the second drawstring contacts and abuts the tapered distal end of the cannula and remains in this position because the slip knot is desirably configured to have a diameter greater than the diameter of the tapered distal end of the cannula. As the second frangible portion is continually pulled, the slide end 32 of the second drawstring is continually pulled with it. The distal loop 33 (not shown) continually becomes smaller, thus resulting in the cinching of the mouth of the pouch. While the mouth of the pouch is being cinched closed, the user concurrently pushes the cannula distally until the slip knot comes into contact with the ovary 43. Alternatively, if a second knot is formed on the distal loop of the drawstring, then the second knot would make this contact.

As illustrated in FIG. 12, once the second drawstring has securely cinched closed the mouth of the pouch about the ovary 43, any excess of the second drawstring can be cut away by cutting, for example, at the second cutting line 45. At this point, the user can then remove the excess thread along with the cannula from the surgical site.

While this invention has been described in its preferred embodiment, numerous alternative embodiments within the scope of the appended claims can be envisioned without departing from the spirit and scope of this invention.

We claim:

1. A medical device for enclosing an internal bodily organ or tissue during surgery comprising a bioabsorbable surgical pouch having first and second drawstrings attached thereon, said pouch having a mouth, said first drawstring being detachable from said pouch and being made of a resilient, biasing thread for biasing the mouth of the pouch open during use, and said second drawstring being made of a compliant, bioabsorbable thread for cinching the mouth of the pouch closed after said organ or tissue is enclosed and means associated with said first drawstring for detaching said first drawstring from said pouch.

2. The device of claim 1 wherein said device further comprises means for cinching the mouth of said pouch closed from a position remote from said surgical pouch.

3. The device of claim 2 wherein the second drawstring has a slide end and a distal loop having a diameter attached about said surgical pouch, and said device is configured to allow for sliding movement of said slide end proximally, causing a continual reduction in the diameter of said distal loop thereby continually cinching the mouth of said pouch closed.

4. The device of claim 3 wherein said pouch is constructed of a warp knit fabric.

5. The device of claim 4 wherein the fabric is characterized by having a density of 8.0 to 15 mg/cm$^2$ and a porosity of 12-20 percent open area.

6. The device of claim 5 wherein the fabric is composed of oxidized regenerated cellulose.

7. The device of claim 6 wherein said distal loop is secured to said slide end of said second drawstring with a slip knot, said slip knot configured to allow sliding movement of said slide end proximally and to prevent said distal loop from loosening when the mouth of said pouch is cinched closed.

8. The device of claim 7 additionally comprising a cannula for mounting the pouch and the first and second drawstrings, said cannula having a proximal end and a distal end wherein said first drawstring has a pulling end for detaching said first drawstring from said pouch, said pulling end being threaded through a cannula and attached within said cannula at the proximal end of said cannula.

9. The device of claim 8 wherein said cannula has a first frangible portion at its proximal end, the first frangible portion having a proximal end and a distal end said first frangible portion having a first score line displayed at the distal end of said first frangible portion to demarcate said first frangible portion.

10. The device of claim 9 wherein said first drawstring has a severing end attached to the distal end of said cannula.

11. The device of claim 10 wherein said slide end of said second drawstring is threaded through said cannula and attached within said cannula at a second frangible portion, said second frangible portion having a proximal end and a distal end said second frangible portion adjacent to and in communication with said first frangible portion.

12. The device of claim 11 wherein said second frangible portion has a second score line display at the distal end of said second frangible portion to demarcate said second frangible portion.

13. The device of claim 12 wherein said first and second drawstrings are threaded through said cannula in separate channels running through said cannula.

14. The device of claim 13 wherein said cannula is tapered at its distal end.

15. The device of claim 14 wherein said slip knot abuts said tapered distal end of said cannula when said slide end of said second drawstring is pulled proximally, and said tapered distal end has a cross-sectional diameter effective to prevent said slip knot from passing through said cannula when said slide end is pulled proximally.

16. The device of claim 15 wherein the mouth of said pouch has a circumference and said pouch further comprises a hem bordering the circumference of the mouth of said pouch, and said first and second drawstrings are threaded through said hem.

17. The device of claim 16 wherein said bioabsorbable thread is selected from the group consisting of a polymer of p-dioxanone, glycolide, lactide, trimethylene carbonate, e-caprolactone, or a copolymer of any of these, and oxidized regenerated cellulose.

18. The device of claim 17 wherein said bioabsorbable thread is a size 4-0 thread.

19. The device of claim 18 wherein said resilient thread is selected from the group consisting of nylon, polyester and polypropylene.

* * * * *